United States Patent
Michelson

(10) Patent No.: US 7,611,536 B2
(45) Date of Patent: *Nov. 3, 2009

(54) HEMI-INTERBODY SPINAL FUSION IMPLANTS MANUFACTURED FROM A MAJOR LONG BONE RING

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 66 days.

This patent is subject to a terminal disclaimer.

(21) Appl. No.: 11/338,395

(22) Filed: Jan. 24, 2006

(65) Prior Publication Data

US 2006/0122702 A1 Jun. 8, 2006

Related U.S. Application Data

(63) Continuation of application No. 10/112,745, filed on Apr. 2, 2002, now Pat. No. 6,989,031.

(60) Provisional application No. 60/281,187, filed on Apr. 3, 2001, provisional application No. 60/281,112, filed on Apr. 2, 2001.

(51) Int. Cl.
*A61F 2/44* (2006.01)

(52) U.S. Cl. .................. 623/17.11; 623/17.16

(58) Field of Classification Search ... 623/17.11–17.16; 606/60, 61, 86 A
See application file for complete search history.

(56) References Cited

U.S. PATENT DOCUMENTS

| | | | |
|---|---|---|---|
| 2,677,369 A | 5/1954 | Knowles | |
| 3,848,601 A | 11/1974 | Ma et al. | |
| 3,867,728 A | 2/1975 | Stubstad et al. | |
| 3,875,595 A | 4/1975 | Froning | |
| 3,905,047 A | 9/1975 | Long | |
| D245,259 S | 8/1977 | Shen | |
| 4,070,514 A | 1/1978 | Eatherly et al. | |
| 4,309,777 A | 1/1982 | Patil | |
| 4,349,921 A | 9/1982 | Kuntz | |
| 4,501,269 A | 2/1985 | Bagby | |
| RE31,865 E | 4/1985 | Roux | |
| 4,599,086 A | 7/1986 | Doty | |
| 4,636,217 A | 1/1987 | Ogilvie et al. | |
| 4,714,469 A * | 12/1987 | Kenna | 606/86 A |
| 4,743,256 A | 5/1988 | Brantigan | |

(Continued)

FOREIGN PATENT DOCUMENTS

EP 0077159 4/1983

(Continued)

OTHER PUBLICATIONS

U.S. Appl. No. 09/593,591, filed Jun. 2000, Michelson.

(Continued)

*Primary Examiner*—Pedro Philogene
(74) *Attorney, Agent, or Firm*—Martin & Ferraro, LLP

(57) ABSTRACT

An interbody spinal implant comprising cortical bone having a width less than one-half the width of the disc space into which it is adapted to be inserted. The implant has a leading end that is asymmetrical from side to side and/or includes a straight portion adapted to be used in side-by-side pairs.

86 Claims, 7 Drawing Sheets

U.S. PATENT DOCUMENTS

| | | | |
|---|---|---|---|
| 4,759,766 | A | 7/1988 | Buettner-Janz et al. |
| 4,759,769 | A | 7/1988 | Hedman et al. |
| 4,820,305 | A | 4/1989 | Harms et al. |
| 4,834,757 | A | 5/1989 | Brantigan |
| 4,863,477 | A | 9/1989 | Monson |
| 4,877,020 | A | 10/1989 | Vich |
| 4,878,915 | A | 11/1989 | Brantigan |
| 4,904,261 | A | 2/1990 | Dove et al. |
| 4,911,718 | A | 3/1990 | Lee et al. |
| 4,936,848 | A | 6/1990 | Bagby |
| 4,955,908 | A | 9/1990 | Frey et al. |
| 5,015,247 | A | 5/1991 | Michelson |
| 5,015,255 | A | 5/1991 | Kuslich |
| 5,047,055 | A | 9/1991 | Bao et al. |
| 5,059,193 | A | 10/1991 | Kuslich |
| 5,062,845 | A | 11/1991 | Kuslich et al. |
| 5,071,437 | A | 12/1991 | Steffee |
| 5,122,130 | A | 6/1992 | Keller |
| 5,123,926 | A | 6/1992 | Pisharodi |
| 5,192,327 | A | 3/1993 | Brantigan |
| 5,246,458 | A | 9/1993 | Graham |
| 5,258,031 | A | 11/1993 | Salib et al. |
| 5,306,308 | A | 4/1994 | Gross et al. |
| 5,306,309 | A | 4/1994 | Wagner et al. |
| 5,370,697 | A | 12/1994 | Baumgartner |
| 5,397,364 | A | 3/1995 | Kozak et al. |
| 5,425,772 | A | 6/1995 | Brantigan |
| 5,443,514 | A | 8/1995 | Steffee |
| 5,458,638 | A | 10/1995 | Kuslich et al. |
| 5,507,813 | A | 4/1996 | Dowd et al. |
| 5,571,109 | A | 11/1996 | Bertagnoli |
| D377,527 | S | 1/1997 | Michelson |
| 5,609,635 | A | 3/1997 | Michelson |
| 5,645,084 | A | 7/1997 | McKay |
| 5,669,909 | A | 9/1997 | Zdeblick et al. |
| 5,683,463 | A | 11/1997 | Godefroy et al. |
| 5,702,449 | A | 12/1997 | McKay |
| 5,766,252 | A | 6/1998 | Henry et al. |
| 5,776,199 | A | 7/1998 | Michelson |
| 5,782,919 | A | 7/1998 | Zdeblick et al. |
| D397,439 | S | 8/1998 | Koros et al. |
| 5,800,547 | A | 9/1998 | Schafer et al. |
| 5,814,084 | A | 9/1998 | Grivas et al. |
| 5,846,484 | A | 12/1998 | Scarborough et al. |
| 5,861,041 | A | 1/1999 | Tienboon |
| 5,865,845 | A | 2/1999 | Thalgott |
| 5,888,222 | A | 3/1999 | Coates et al. |
| 5,888,226 | A | 3/1999 | Rogozinski |
| 5,888,227 | A | 3/1999 | Cottle |
| 5,899,939 | A | 5/1999 | Boyce et al. |
| 5,906,635 | A | 5/1999 | Maniglia |
| 5,972,368 | A | 10/1999 | McKay |
| 5,989,289 | A | 11/1999 | Coates et al. |
| 6,033,438 | A * | 3/2000 | Bianchi et al. ............ 623/17.16 |
| 6,037,519 | A | 3/2000 | McKay |
| 6,039,762 | A | 3/2000 | McKay |
| D425,989 | S | 5/2000 | Michelson |
| 6,083,228 | A | 7/2000 | Michelson |
| 6,111,164 | A | 8/2000 | Rainey et al. |
| 6,113,638 | A | 9/2000 | Williams et al. |
| 6,136,031 | A | 10/2000 | Middleton |
| 6,143,032 | A | 11/2000 | Schafer et al. |
| 6,159,214 | A | 12/2000 | Michelson |
| 6,174,311 | B1 * | 1/2001 | Branch et al. ................. 606/61 |
| 6,179,875 | B1 | 1/2001 | Von Strempel |
| 6,200,347 | B1 | 3/2001 | Anderson et al. |
| 6,206,923 | B1 | 3/2001 | Boyd et al. |
| 6,224,607 | B1 | 5/2001 | Michelson |
| 6,231,610 | B1 | 5/2001 | Geisler |
| 6,241,770 | B1 | 6/2001 | Michelson |
| 6,241,771 | B1 | 6/2001 | Gresser et al. |
| 6,245,108 | B1 | 6/2001 | Biscup |
| 6,258,125 | B1 * | 7/2001 | Paul et al. ................. 623/17.11 |
| 6,261,586 | B1 | 7/2001 | McKay |
| 6,270,528 | B1 | 8/2001 | McKay |
| 6,277,149 | B1 | 8/2001 | Boyle et al. |
| 6,294,041 | B1 | 9/2001 | Boyce et al. |
| 6,294,187 | B1 | 9/2001 | Boyce et al. |
| 6,342,074 | B1 | 1/2002 | Simpson |
| 6,348,071 | B1 | 2/2002 | Steffee et al. |
| 6,350,283 | B1 | 2/2002 | Michelson |
| 6,371,988 | B1 | 4/2002 | Pafford et al. |
| 6,383,221 | B1 | 5/2002 | Scarborough et al. |
| 6,391,058 | B1 | 5/2002 | Kuslich et al. |
| 6,395,031 | B1 | 5/2002 | Foley et al. |
| 6,402,785 | B1 | 6/2002 | Zdeblick et al. |
| 6,409,765 | B1 | 6/2002 | Bianchi et al. |
| 6,423,095 | B1 | 7/2002 | Van Hoeck et al. |
| 6,468,311 | B2 | 10/2002 | Boyd et al. |
| 6,471,724 | B2 | 10/2002 | Zdeblick et al. |
| 6,482,233 | B1 | 11/2002 | Aebl et al. |
| 6,511,509 | B1 | 1/2003 | Ford et al. |
| 6,530,955 | B2 | 3/2003 | Boyle et al. |
| 6,554,863 | B2 | 4/2003 | Paul et al. |
| 6,562,072 | B1 | 5/2003 | Fuss et al. |
| 6,572,654 | B1 | 6/2003 | Santilli |
| 6,629,998 | B1 | 10/2003 | Lin |
| 6,635,086 | B2 | 10/2003 | Lin |
| 6,706,067 | B2 | 3/2004 | Shimp et al. |
| 6,749,636 | B2 | 6/2004 | Michelson |
| 6,808,585 | B2 | 10/2004 | Boyce et al. |
| 6,827,740 | B1 | 12/2004 | Michelson |
| 6,890,355 | B2 | 5/2005 | Michelson |
| 6,989,031 | B2 * | 1/2006 | Michelson ............... 623/17.11 |
| 7,048,762 | B1 * | 5/2006 | Sander et al. ............ 623/17.11 |
| 7,087,082 | B2 | 8/2006 | Paul et al. |
| 7,115,146 | B2 * | 10/2006 | Boyer et al. ............. 623/23.63 |
| 2001/0018614 | A1 | 8/2001 | Bianchi |
| 2001/0031254 | A1 | 10/2001 | Bianchi et al. |
| 2002/0091447 | A1 | 7/2002 | Shimp et al. |
| 2002/0099444 | A1 | 7/2002 | Boyd et al. |
| 2002/0107571 | A1 | 8/2002 | Foley |
| 2003/0028249 | A1 | 2/2003 | Baccelli et al. |

FOREIGN PATENT DOCUMENTS

| | | |
|---|---|---|
| EP | 0179695 | 4/1986 |
| EP | 0307241 | 3/1989 |
| EP | 0577179 | 1/1994 |
| EP | 0599419 | 6/1994 |
| EP | 2703580 | 10/1994 |
| EP | 0627204 | 12/1994 |
| EP | 0637440 | 11/1997 |
| JP | 57/029348 | 9/1982 |
| JP | 62/155846 | 7/1987 |
| WO | WO 93/01771 | 2/1993 |
| WO | WO 95/08306 | 3/1995 |
| WO | WO 95/08964 | 4/1995 |
| WO | WO 96/22747 | 8/1996 |
| WO | WO 99/63891 | 12/1999 |
| WO | WO 00/07527 | 2/2000 |
| WO | WO 00/74608 | 12/2000 |
| WO | WO 01/28465 | 4/2001 |
| WO | WO 01/68005 | 4/2001 |
| WO | WO 01/62191 | 8/2001 |
| WO | WO 01/68004 | 9/2001 |

OTHER PUBLICATIONS

DeBowes, R.M., et al.; Study of Bovine . . . Steel Baskets; Transactions of the 29th Annual Meeting; Orthopedic Research Society, vol. 8, p. 407, Mar. 8-10, 1983.

Otero-Vich, Jose M.; Anterior Cervical Interbody Fusion with Threaded Cyllnrical Bone; J. Neurosurg 63:750-753 (Nov. 1985).

Schmitz et al.; Performance of Alloplastic Materials and Design of an Artificial Disc; the Artificial Disc. Brock, Mayer, Weigel; pp. 23-34(1991).

Zindrick, et al.; Lumbar Spine Fusion: Different Types and Indications; The Lumbar Spine, vol. 1. Second Edition, pp. 588-593(1996).

Crock, H.V.; Practice of Spinal Surgery; Springer-Verlag/Wien, New York (1983).

Itoman, M., et al.; Banked Bone grafting for Bone Defect Repair-Clinical Evaluation of Bone Union and Graft Incorporation; J. Jpn. Orthop. Assoc. 62:461-469(1988).

Laparoscopic Bone Dowel Surgical Technique; Brochure of Sofamor Danek (1995).

Brochure of University of Florida Tissue Bank; MD-I and MD-II Custom Machine Cortical Dowels; (*Circa* 1996).

Brochure of University of Florida Tissue Bank; MD-III Threaded Cortical Dowel; (*Circa* 1996).

Ray, C.D.; Spinal Interbody Fusions: A Review, Featuring New Generation Techniques; Neurosurgery Quarterly, 7(2):135-156 (1997).

A picture of a Medtronic, Sofamor Danek Display; titled "Evolving With Your Needs" (Apr. 2000).

RTI Precision Machined Allograft: The Surgeon's Choice, Brochure by Regeneration Technologies, Inc. (2000).

Puros ALIF Bone Graft, Brochure by Sulzer Spine-Tech (2001).

What's New at . . . Spine-Tech: Allograft and Thoracolumbar, Brochure Spine-Tech (*Circa* 2001).

New IBS Allograft, The C-TLIF Approach, Brochure of OrthoDevelopment (2002).

Introducing graftech Allografts, Webpage by Osteotech (*Circa* Jan. 2002).

RTI Tissue Services, Spinal Allograft, Webpage of Regeneration Technologies, Inc. (2002).

Muschler, et al.; The Biology of Spinal Fusion; Spinal Fusion Science and Technique, Cotler and Cotler, pp. 9-13 (1990); prior to Apr. 2, 2001.

\* cited by examiner

FIG. 1
*PRIOR ART*
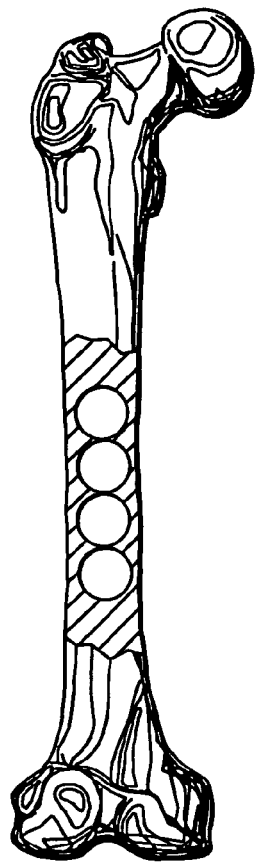
FIG. 2
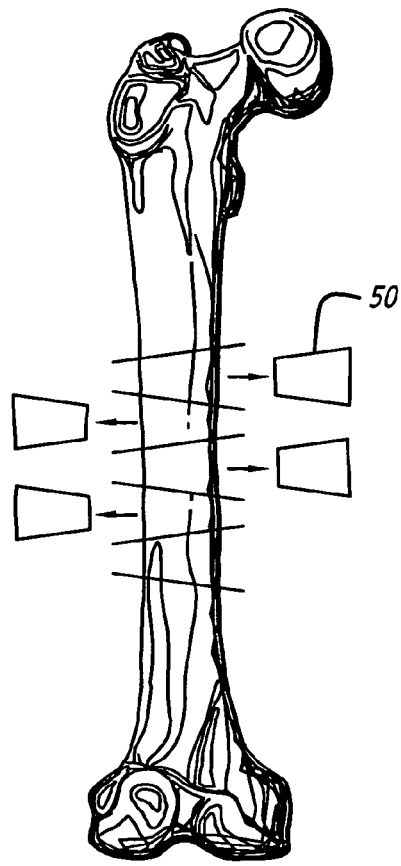
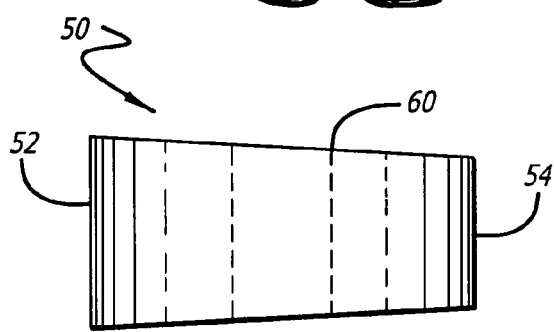
FIG. 3
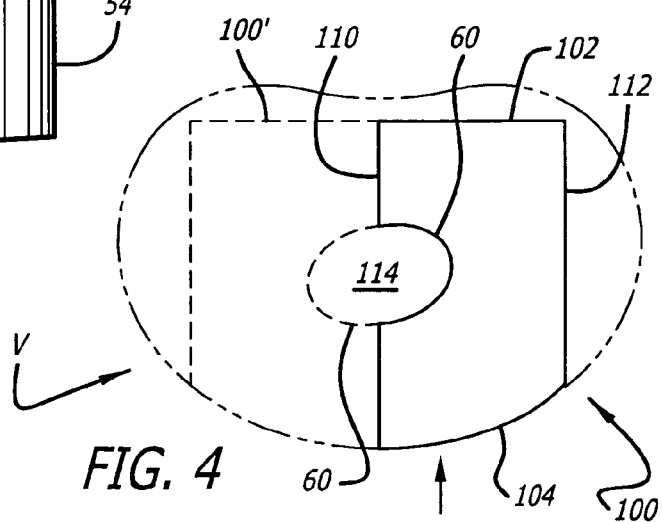
FIG. 4

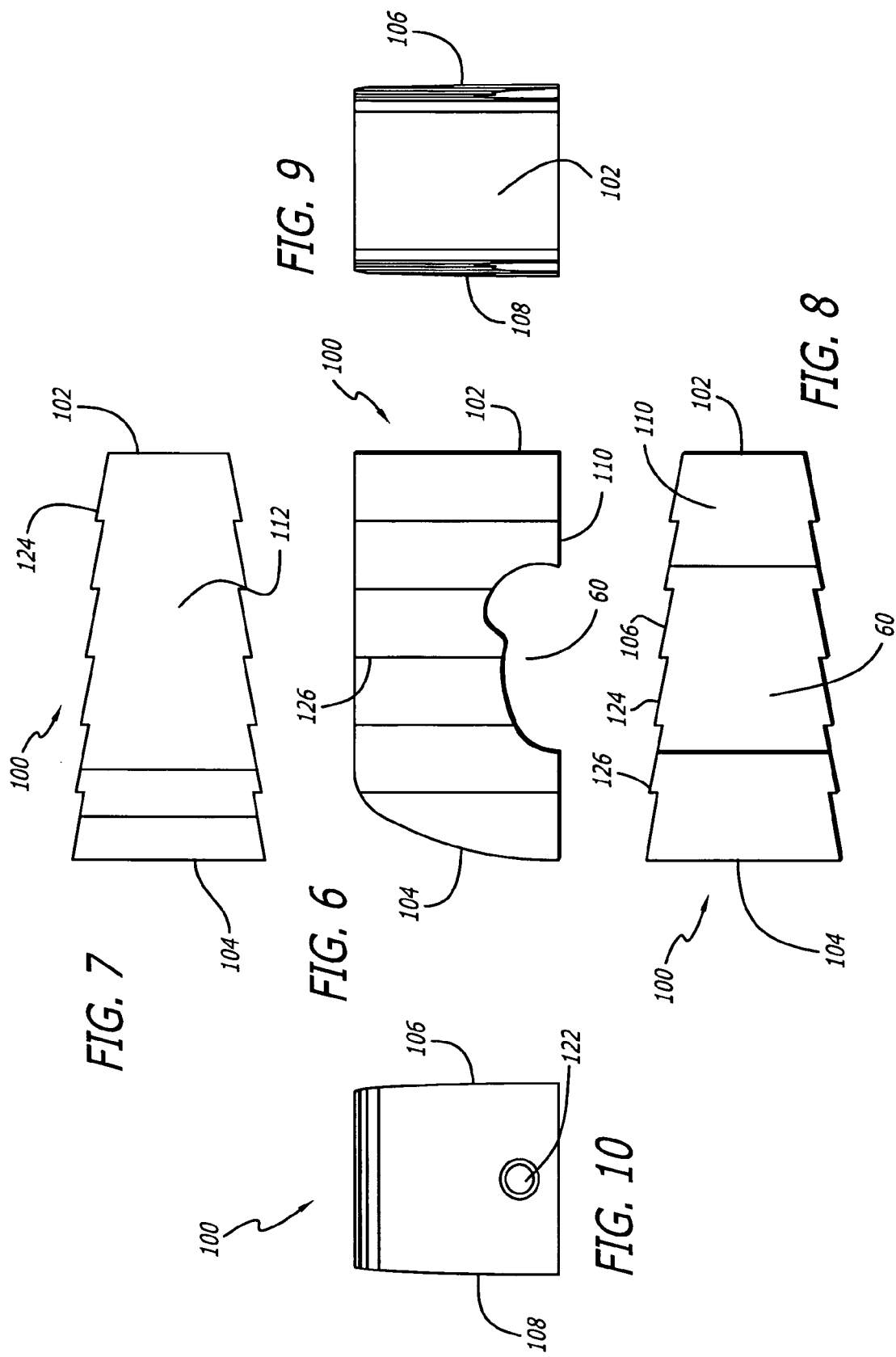

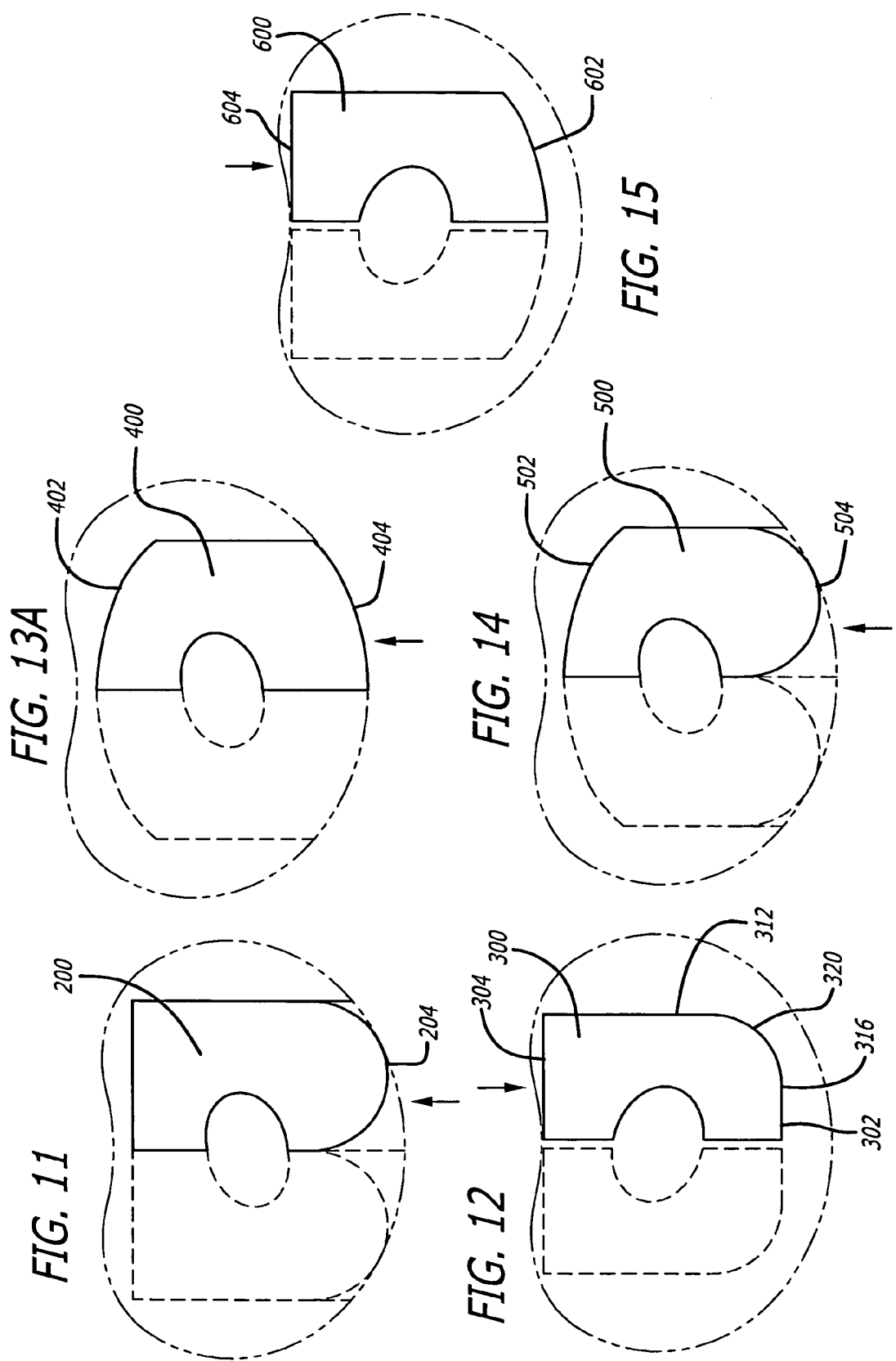

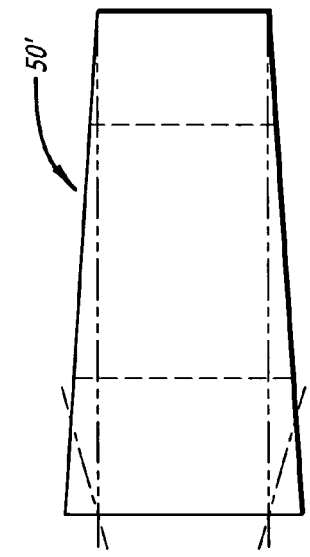
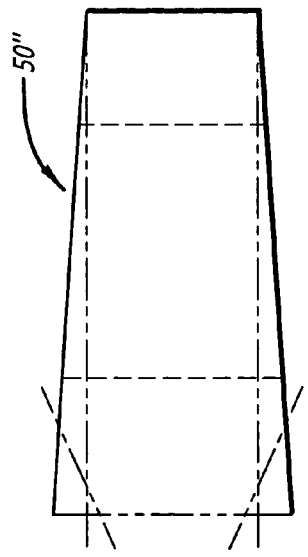
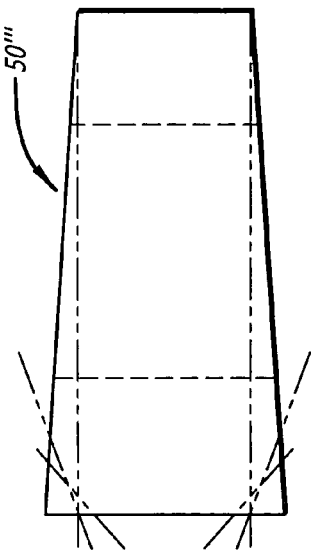
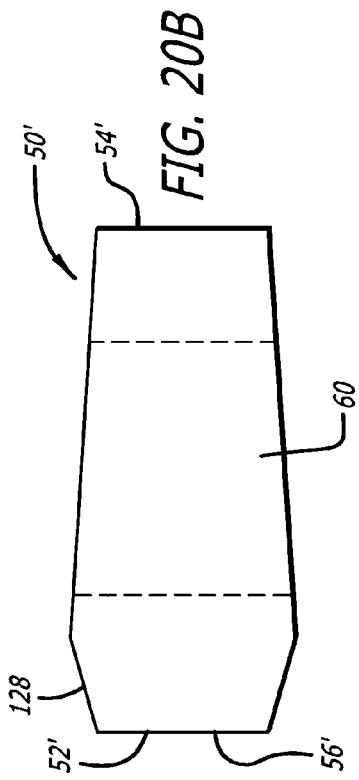
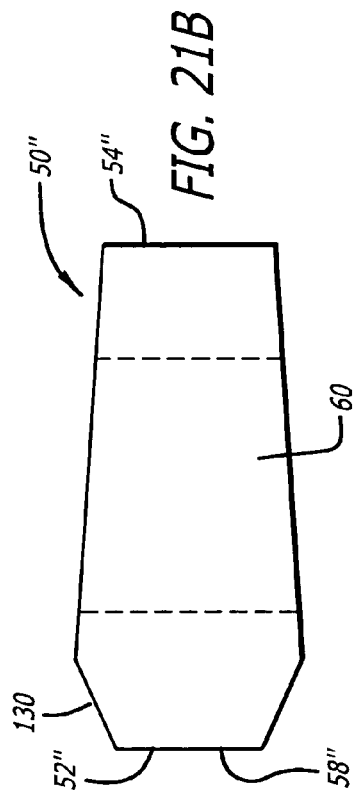
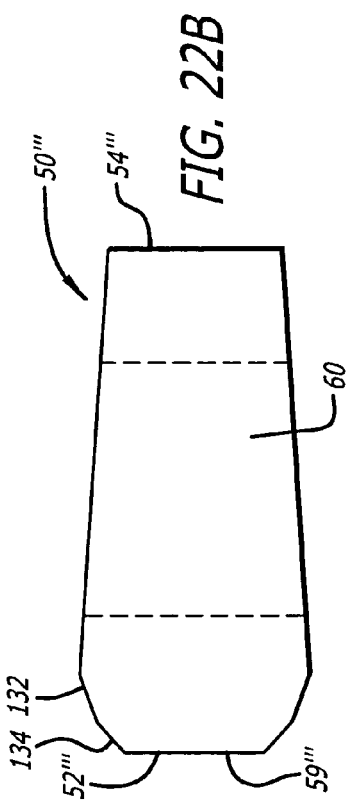

HEMI-INTERBODY SPINAL FUSION IMPLANTS MANUFACTURED FROM A MAJOR LONG BONE RING

RELATED APPLICATIONS

This application is a continuation of U.S. application Ser. No. 10/112,745, filed Apr. 2, 2002 now U.S. Pat. No. 6,989,031; which claims priority to U.S. Provisional Application No. 60/281,187, filed Apr. 3, 2001, and U.S. Provisional Application No. 60/281,112, filed Apr. 2, 2001; all of which are incorporated by reference herein.

BACKGROUND

Description of the Related Art

The diaphysis is the shaft of a major long bone between the epiphyses, the ends of the bone forming the joints. Human cadaveric diaphyseal bone is used to form implants made of bone utilized in interbody spinal fusion surgery.

As show in FIG. 1, interbody spinal implants in the form of bone dowels can be formed by making circular cuts transverse to the long axis of the diaphysis. The circular cuts required to form cylindrical bone dowels create unusable portions of the diaphyseal bone and is not an efficient use of a precious and scarce resource.

As shown in FIG. 2, a diaphyseal ring is formed by making two spaced apart cuts approximately perpendicular to the long axis of the diaphyseal portion of a major long bone with the medullary canal forming an opening through the ring. Such rings are generally harvested from femurs for use in the lumbar spine. Other bones from the arm or leg or other part of the human skeleton may be useful in various regions of the spine.

The cuts are generally spaced apart so as to form a ring of bone having a height corresponding to the restored disc space or slightly greater. Diaphyseal ring bone grafts are placed into the spine within and across the height of the space previously occupied by a spinal disc between adjacent vertebral bodies to achieve interbody fusion of those vertebral bodies through the disc space. The diaphyseal ring bone graft is incorporated into the bony fusion over time.

Interbody spinal fusion with diaphyseal bone rings, however, has had limited success in the past. While all the causes for failure may not yet be appreciated, it is nevertheless believed that a failure to gain congruity at the interfaces of the bone ring implant to the adjacent vertebral bodies, and a failure to achieve stability of the bone ring implant, may be two of the more significant factors subject to the surgeon's control contributing to such failures. Moreover, bone rings are limited to insertion from an anterior approach to the spine and require a relatively large incision for insertion.

Interbody spinal implants that are entirely or almost entirely made of cortical bone or a bone composite material offer the advantages of that material including an appropriate modulus of elasticity and strength for the prescribed use, the capacity to be bioactive, including being osteoconductive, osteoinductive, osteogenic, and to more generally provide a good substrate for the formation of new bone as fusion occurs. Further, by being bioabsorable the bone material is replaced by the patient's own bone over time, thereby preventing stress shielding and leading to the eventual elimination of any foreign body from the implantation site.

As it is desirable to take advantage of all these benefits, there exists a need for an improved interbody spinal fusion implant made of bone or a bone composite material having a configuration that provides for an improved congruity of the implant to the vertebral bodies and improved implant stability, that is adapted for insertion from either an at least in part anterior or posterior approach to the spine, and is adapted to be inserted through a relatively small incision.

SUMMARY OF THE INVENTION

In accordance with the purposes of the present invention, as embodied and broadly described herein, an interbody spinal fusion implant made of cortical bone is provided for insertion at least in part into an implantation space formed across the height of a disc space between adjacent vertebral bodies of a human spine. The implant includes a leading end for insertion first into the disc space, a trailing end opposite the leading end, and a length along a mid-longitudinal axis of the implant. The leading end has a generally straight portion from side to side. The implant also includes opposed upper and lower portions between the leading and trailing ends that are adapted to be placed within the disc space to contact and support the adjacent vertebral bodies. The upper and lower portions are non-arcuate along at least a portion of the length of the implant. The implant also includes an interior facing side, an exterior facing side opposite the interior side, and a maximum width therebetween. The maximum width of the implant is less than approximately one-half of the width of the adjacent vertebral bodies into which the implant is adapted to be inserted. The interior and exterior sides connect the upper and lower portions and the leading and trailing ends. The interior side forms a corner with the generally straight portion of the leading end. The interior side is adapted to be oriented toward an interior side of another implant when inserted within the disc space.

The implant is preferably manufactured from a bone ring obtained from a major long bone of a human having a medullary canal. The interior side of the implant includes at least a portion of the medullary canal so that when the implant is placed side by side another implant having an interior side with at least a portion of a medullary canal, a passage is formed. The passage is adapted to hold bone growth promoting material to permit for the growth of bone from vertebral body to vertebral body through the passage.

In another preferred embodiment, the implant is manufactured from a bone composite material. The interior side includes a recess so that when the implant is placed side by side another implant having an interior side including a recess, a passage is formed. The passage is adapted to hold bone growth promoting material to permit for the growth of bone from vertebral body to vertebral body through the implant.

In accordance with the purposes of another embodiment of the present invention, as embodied and broadly described herein, an interbody spinal fusion implant made of cortical bone is provided for insertion at least in part into an implantation space formed across the height of a disc space between adjacent vertebral bodies of a human spine. The implant has a leading end that is asymmetrical from side to side. The implant is manufactured from a bone ring obtained from a major long bone of a human and includes at least 40 percent of the bone ring from which it is being formed.

In accordance with the purposes of a further embodiment of the present invention, as embodied and broadly described herein, a pair of interbody spinal fusion implants manufactured from a bone composite material is provided for insertion at least in part into an implantation space formed across the height of a disc space between adjacent vertebral bodies of a human spine. Each implant has a length that is greater than one half the depth of the vertebral bodies adjacent the disc space into which the implant is adapted to be inserted. Each implant has a leading end that is asymmetrical from side to side. Each implant has an interior facing side that includes a recess to form a passage when the implants are placed side by side with the interior sides facing each other. The combined width of the pair of implants is greater than one half the width of the adjacent vertebral bodies into which the implants are adapted to be inserted.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

FIG. 1 is a side elevation view of a human long bone in partial cross section illustrating the harvesting of cylindrical dowels of diaphyseal bone.

FIG. 2 is a side elevation view of a human long bone illustrating the harvesting of diaphyseal bone rings in accordance with the present invention.

FIG. 3 is a side elevation view of a diaphyseal bone ring in accordance with a preferred embodiment of the present invention.

FIG. 4 is a top plan view of a preferred embodiment of a bone implant in accordance with the present invention and a second bone implant that is a mirror image thereof illustrated in dashed line, both implants being shown implanted from an anterior approach to the spine in a vertebral body illustrated in dashed line.

FIG. 6 is a top plan view of one of the implants of FIG. 5.

FIG. 7 is an exterior side elevation view of the implant of FIG. 6.

FIG. 8 is an interior side elevation view of the implant of FIG. 6.

FIG. 9 is a leading end view of the implant of FIG. 6.

FIG. 10 is a trailing end view of the implant of FIG. 6.

FIG. 11 is a top plan view of another preferred embodiment of a bone implant in accordance with the present invention and a second bone implant that is a mirror image thereof illustrated in dashed line, both implants being shown implanted from an anterior approach to the spine in a vertebral body illustrated in dashed line.

FIG. 12 is a top plan view of another preferred embodiment of a bone implant in accordance with the present invention and a second bone implant that is a mirror image thereof illustrated in dashed line, both implants being shown implanted from a posterior approach to the spine in a vertebral body illustrated in dashed line.

FIG. 13A is a top plan view of another preferred embodiment of a bone implant in accordance with the present invention and a second bone implant that is a mirror image thereof illustrated in dashed line, both implants being shown implanted from an anterior approach to the spine in a vertebral body illustrated in dashed line.

FIG. 14 is a top plan view of another preferred embodiment of a bone implant in accordance with the present invention and a second bone implant that is a mirror image thereof illustrated in dashed line, both implants being shown implanted from an anterior approach to the spine in a vertebral body illustrated in dashed line.

FIG. 15 is a top plan view of another preferred embodiment of a bone implant in accordance with the present invention and a second bone implant that is a mirror image thereof illustrated in dashed line, both implants being shown implanted from a posterior approach to the spine in a vertebral body illustrated in dashed line.

FIG. 20A is a side elevation view of a section of diaphyseal bone cut across the longitudinal axis of a long bone illustrating a method of forming a shape of an implant in accordance with a preferred embodiment of the present invention.

FIG. 20B is a side elevation view of an implant in accordance with a preferred embodiment of the present invention formed by the method of FIG. 20A.

FIG. 21A is a side elevation view of a section of diaphyseal bone cut across the longitudinal axis of a long bone illustrating a method of forming a shape of an implant in accordance with another preferred embodiment of the present invention.

FIG. 21B is a side elevation view of an implant in accordance with another preferred embodiment of the present invention formed by the method of FIG. 21A.

FIG. 22A is a side elevation view of a section of diaphyseal bone cut across the longitudinal axis of a long bone illustrating a method of forming a shape of an implant in accordance with another preferred embodiment of the present invention.

FIG. 22B is a side elevation view of an implant in accordance with another preferred embodiment of the present invention formed by the method of FIG. 22A.

DETAILED DESCRIPTION OF THE DRAWINGS

Figure 5:
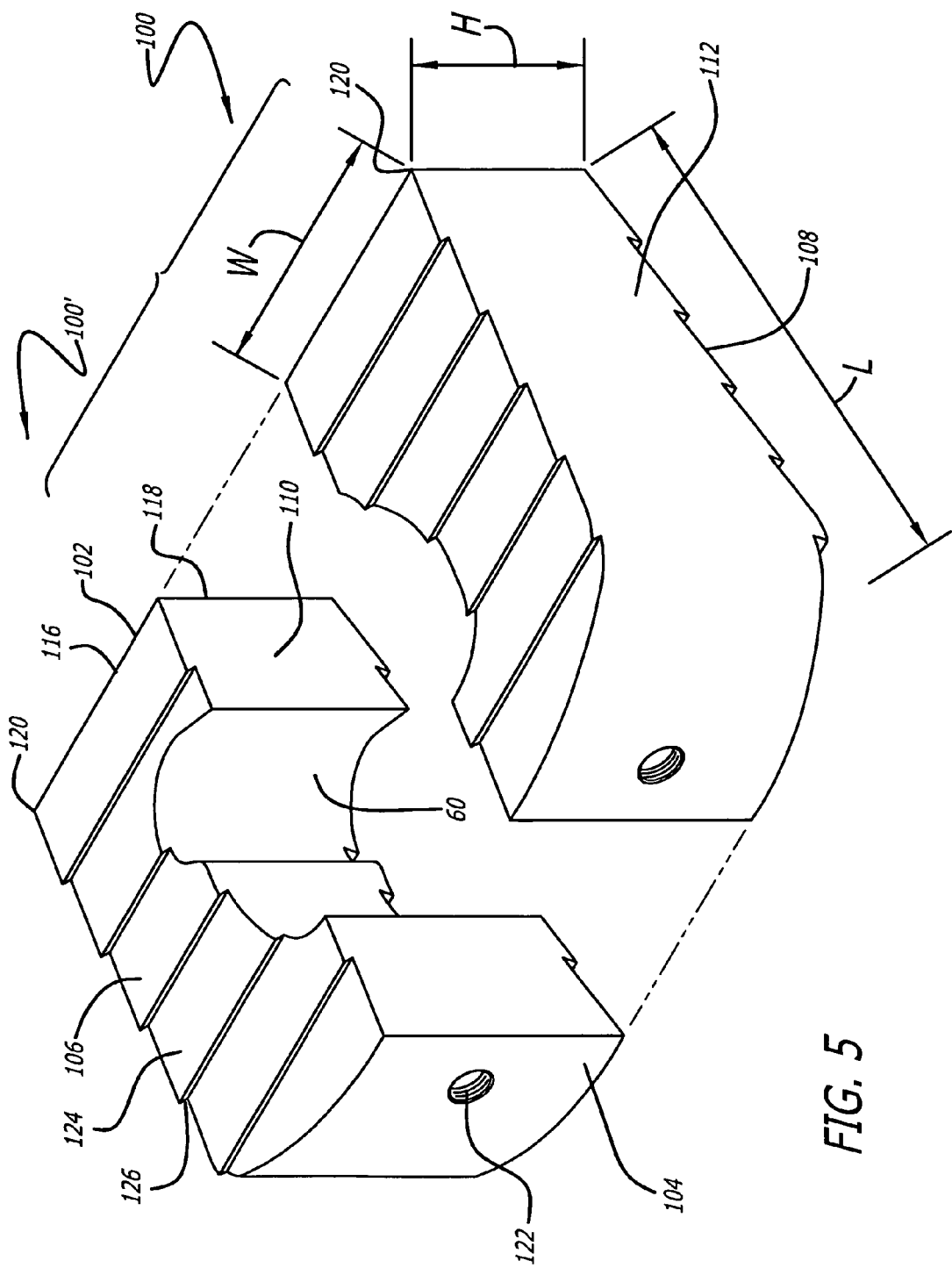
FIG. 5 is a rear perspective view of the implants of FIG. 4.

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings. Wherever possible, the same reference numbers will be used throughout the drawings to refer to the same or like parts.

FIGS. 2 and 3 show a preferred method for obtaining a diaphyseal bone ring 50 from a major long bone used to form certain of the implants of the present invention. Bone ring 50 is formed by making two spaced apart cuts approximately perpendicular to the long axis of the diaphyseal portion of a major long bone with a portion of the medullary canal forming an opening through the ring. Such rings are generally harvested from femurs for use in the lumbar spine. Other bones from the arm or leg or other part of the human skeleton may be useful in various regions of the spine. The cuts may be made into the long bone generally perpendicular to or at other angles transverse to the long axis of the diaphyseal bone to form bone ring 50 having upper and lower surfaces. Making the cuts at an angle to each other creates a bone ring with upper and lower surfaces that are angled relative to each other. The angular relationship of the upper and lower surface of the bone ring, when subsequently formed into an implant and implanted into the spine, positions the adjacent vertebral bodies in angular relationship to each other to restore the natural curvature of the spine, such as lordosis for example.

As shown in FIG. 3, bone ring 50 has an end 52 with a height that is greater than the height at an end 54. Bone ring 50 also has a medullary canal 60 therethrough, shown in outline.

Where it is desired to form two implants from a bone ring, bone ring 50 may be cut into two parts, each part including at least a portion of the medullary canal. Thereafter, the parts are machined to form a desired shape suitable for their intended use as an interbody spinal implant. Examples of tools which may be used to machine the implant include, but are not limited to, burrs, reamers, mills, saws, trephines, chisels, and the like. Each part of the bone may be machined to form an implant having a leading end. For example only, the leading end may be shaped to be asymmetrical from side to side and/or may have a straight portion from side to side at the leading end. The interior side includes at least a portion of the medullary canal and may be machined to be at least in part straight. The exterior side also may be machined to have a straight portion. The trailing end of each part may be machined to any desired shape suitable for the intended purpose and may be shaped to conform to the anatomical contour of the adjacent vertebral bodies between which the implant is adapted to be inserted. Where it is appropriate, it may be desirable to preserve at least a portion of the natural curvature of the perimeter of the bone ring as part of the configuration of the implant shape.

FIGS. 4-10 show an implant 100 in accordance with a preferred embodiment of the present invention adapted for use from an anterior approach to the spine. Implant 100 has a leading end 102 for insertion first into the disc space between two adjacent vertebral bodies and a trailing end 104 opposite leading end 102. Implant 100 has an upper portion 106, a lower portion 108, an interior side 110, and an exterior facing side 112 opposite interior facing side 110. As used herein, the phrase "interior side" describes the side of the implant adapted to be orientated toward the interior side of another implant when a pair of implants are inserted side by side into the disc space. Interior side 110 includes at least a portion of the medullary canal of the bone ring.

FIG. 4 shows a top plan view of a vertebral body V and implants 100 and 100', respectively, inserted from an anterior approach to the spine. Implant 100' is preferably, but need not be, a mirror image of implant 100. The description of implant 100 is equally applicable to implant 100'. Implant 100 is placed side by side with implant 100' so that the portions of the medullary canal of interior sides 110 of each implant are positioned adjacent one another to form a passage 114 therethrough. Preferably passage 114 is adapted to hold bone growth promoting material to permit for the growth of bone from vertebral body to vertebral body through passage 114. Preferably, the combined width of both implants is greater than one-half the width of the adjacent vertebral bodies into which the implants are adapted to be inserted.

In a preferred embodiment of the present invention, leading end 102 and opposed sides 110, 112 are machined to have various configurations. Leading end 102 can be machined to have a generally planar configuration across at least a portion of its width from side to side. For example, leading end 102 is preferably machined to have a generally straight portion 116 from side to side that is preferably oriented at approximately 90° to the mid-longitudinal axis of the implant. Where the implantation space is prepared into the vertebral bodies to have a lip or ridge that is at least in part flat, straight portion 116 may be adapted to abut that portion of the implantation space. Interior side 110 is preferably machined to form a corner 118 with generally straight portion 116 of leading end 102. Exterior side 112 may be machined to form a corner 120 with generally straight portion 116 of leading end 102 or implant 100 may be machined to have a curved transition from straight portion 116 of leading end 102 to exterior side 112. In a preferred embodiment, corners 118, 120 can be machined so either or both of sides 110, 112 are at a 90° angle to straight portion 116 of leading end 102 to produce at least in part straight portions outwardly facing and at least in part generally parallel to each other, that can be aligned or offset from each other along sides 110, 112. One or both of sides 110, 112 may also be formed to be at least in part oriented generally parallel to the mid-longitudinal axis of implant 100. Forming the implant to have a leading end with a straight portion and an interior facing side with a straight portion permits the implant to be placed in proximity to another implant to achieve a better fill of the implantation space. Further, leading end 102 may be tapered to facilitate insertion of implant 100 between the two adjacent vertebral bodies.

An example of an implantation space adapted to receive at least a portion of implant 100 may be preferably formed with the apparatus and method described by Michelson in U.S. Pat. Nos. 6,159,214 and 6,224,607, the disclosures of which are incorporated herein by reference. The instruments and method are not the subject matter of this application. It is understood that the preparation of the implantation space shown therein are a preferred instrument and method of preparing the implantation spaces and that any method and instrumentation suitable for the purpose may be utilized to prepare the desired implantation space.

In a preferred embodiment of implant 100, trailing end 104 preferably has an asymmetrical curvature from side to side, at least a portion of which is preferably adapted to conform to at least a portion of the peripheral contour of the anterior aspect of the vertebral bodies adjacent the disc space into which the implant is inserted.

FIGS. 5 and 10 show that implant 100 preferably has a driver opening 122 at trailing end 104 for cooperatively engaging an instrument for installing implant 100 into the implantation space. Driver opening 122 is preferably configured for threaded engagement with an insertion instrument.

FIGS. 5, 7, and 8 show at least a portion of upper and lower surfaces 106, 108 in an angular relationship to each other from trailing end 104 to leading end 102 for allowing for angulation of the adjacent vertebral bodies relative to each other. Preferably, upper and lower surfaces 106, 108 are non-arcuate in a direction along the longitudinal axis of implant 100. In addition to passage 114, upper and lower surfaces 106, 108 may include at least one opening in communication with one another to permit for the growth of bone from vertebral body to vertebral body through implant 100, though the invention is not so limited. Upper and lower surfaces 106, 108 may also be porous and may include a bone ingrowth surface.

As shown in FIGS. 5-8, the implants described herein may include a bone-engaging surface 124. Bone engaging surface 124 preferably has forward facing ratchets 126 facing leading end 102 of implant 100. Forward facing ratchets 126 resist motion of implant 100 in a direction opposite to the direction of insertion. Other preferred embodiments of bone-engaging surfaces may include the surfaces of the implant being roughened, knurled, splined, or may include at least one protrusion to penetrably engage the bone of the vertebral bodies. By way of example only, the implants of the present invention may include the surface configuration taught by Michelson in U.S. patent application Ser. No. 09/457,228, entitled "Spinal Implant Surface Configuration," the disclosure of which is incorporated by reference herein.

Implant 100 is preferably manufactured from a bone ring 50 and includes approximately 40 percent or more of the bone ring from which it is formed. Implant 100 preferably has a length L greater than one-half the depth of the vertebral bodies adjacent the disc space into which the implant is adapted to be inserted as measured between the anterior and posterior aspects of the vertebral bodies. Implant 100 also preferably has a maximum width W that is less than approximately one-half the width of the adjacent vertebral bodies into which the implant is adapted to be inserted.

For any of the embodiments of the implants of the present invention, instead of being machined from a single bone portion such as bone ring 50, the implant can be manufactured from a composite bone material which may include at least one of cortical bone fibers, bone filaments, bone particles, or bone dust, and a material which may or may not be bioactive and/or bioresorbable such as a plastic, ceramic, for example. By way of example only and not limitation, bioresorbable materials may include polygalactone. Once formed, the composite implant material may be machined or molded, into the desired shape.

FIG. 11 shows an implant 200 in accordance with another preferred embodiment of the present invention adapted for use from an anterior approach to the spine. Implant 200 is similar to implant 100, except that it has a trailing end 204 that is curved from side to side. For example, trailing end 204 may be configured in the shape of a half circle from side to side or may be an arc of a circle. Such a configuration of trailing end does not significantly protrude from the disc space between the vertebral bodies and interfere with any delicate neurostructures or vessels that may be present adjacent thereto.

FIG. 12 shows an implant 300 in accordance with another preferred embodiment of the present invention adapted for use from a posterior approach to the spine. Implant 300 is similar to implant 100 and has a curved transition from straight portion 316 of leading end 302 to exterior side 312 to form a rounded portion 320. Trailing end 304 is at least in part straight and can form a corner with exterior side 312. Trailing end 304 may have other configurations suitable for its intended purpose.

Figure 13B:
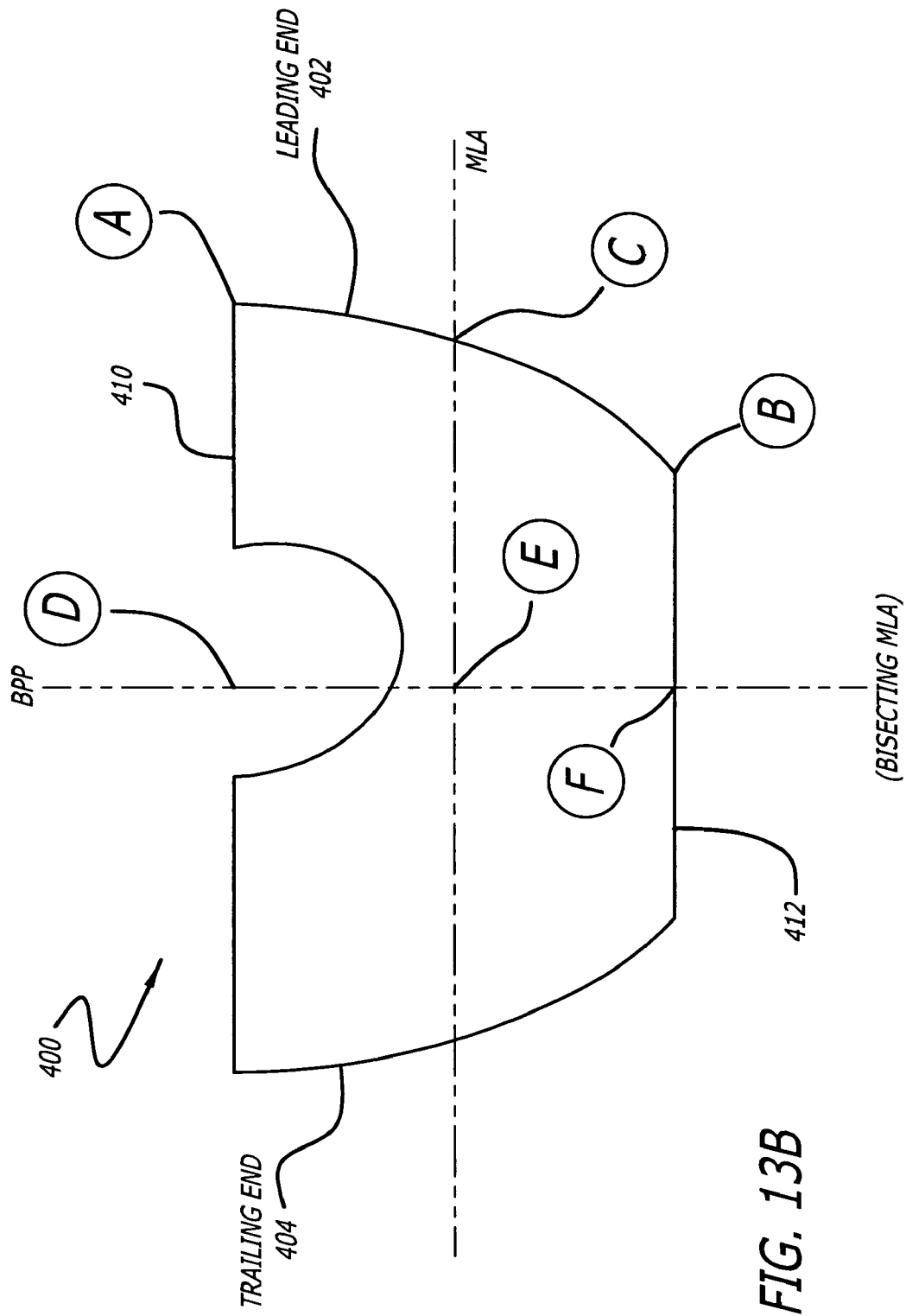
FIG. 13B is a top plan view of the implant of FIG. 13A illustrating the mid-longitudinal axis and a plane bisecting the mid-longitudinal axis along the length of the implant.

FIGS. 13A and 13B show an implant 400 in accordance with another preferred embodiment of the present invention adapted for use from an anterior approach to the spine. Implant 400 has a leading end 402 that is asymmetrical from side to side. An example of an implant having an asymmetric leading end is disclosed by Michelson in U.S. Pat. No. 6,350,282, incorporated by reference herein.

As illustrated in FIG. 13B, implant 400 has a mid-longitudinal axis MLA along its length. Mid-longitudinal axis MLA is shown bisected by a plane BPP perpendicular to and bisecting the length of implant 400 along the mid-longitudinal axis MLA. Implant 400 has a first distance as measured from point C at leading end 402 to plane BPP at point E that is greater than a second distance as measured from plane BPP at point F to the junction of leading end 402 and exterior side 412 at point B. Implant 400 has a third distance as measured from point A at the junction of leading end 402 and interior side 410 to plane BPP at point D that is greater than the second distance as measured from at point F to point B. While in the preferred embodiment as shown in FIG. 13B, the third distance from points A to D is illustrated as being longer than the first distance from points C to E, the third distance can be equal to or less than the first distance. In a preferred embodiment, the first distance measured from points C to E is greater than the second distance measured from points B to F; the third distance measured from points A to D can be less than the first distance measured from points C to E; and the third distance measured from points A to D does not equal the second distance measured from points B to F. Implant 400 preferably has a trailing end 404 that is asymmetrical from side to side. Trailing end 404 may have other configurations suitable for its intended purpose.

FIG. 14 shows an implant 500 in accordance with another preferred embodiment of the present invention adapted for use from an anterior approach to the spine. Implant 500 is similar to implant 400, except that it has a trailing end 504 that is symmetrical side to side. For example, trailing end 504 may be configured in the shape of a half circle from side to side or may be an arc of a circle.

FIG. 15 shows an implant 600 in accordance with another preferred embodiment of the present invention adapted for use from a posterior approach to the spine. Implant 600 is similar to implant 400 except that trailing end 604 is at least in part straight.

Figure 16:
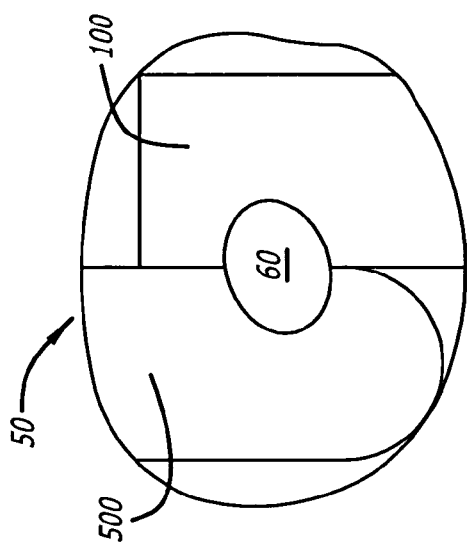
FIG. 16 is a top plan view of a section of diaphyseal bone ring cut across the longitudinal axis of a long bone illustrating the shapes of two implants that can be formed therefrom in accordance with a preferred embodiment of the present invention.
Figure 17:
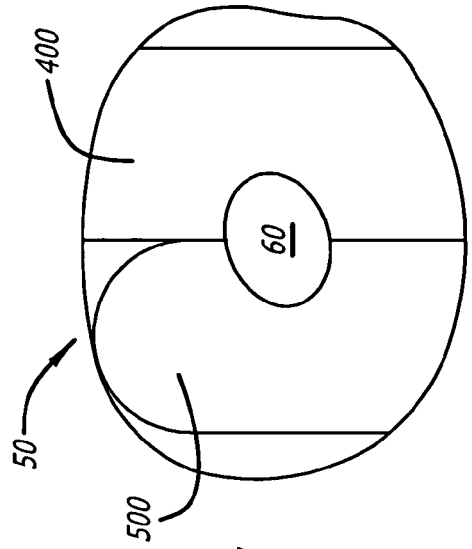
FIG. 17 is a top plan view of a section of diaphyseal bone ring cut across the longitudinal axis of a long bone illustrating the shapes of two implants that can be formed therefrom in accordance with another preferred embodiment of the present invention.
Figure 18:
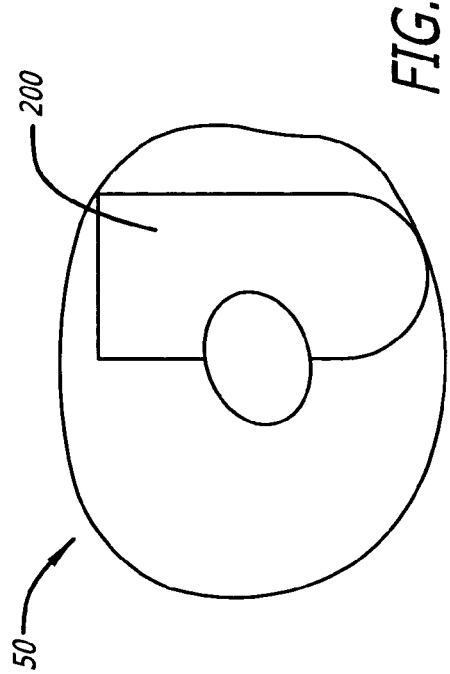
FIG. 18 is a top plan view of a section of diaphyseal bone ring cut across the longitudinal axis of a long bone illustrating the shapes of two implants that can be formed therefrom in accordance with another preferred embodiment of the present invention.

FIGS. 16-19 each show a top plan view of a section of diaphyseal bone ring 50 cut across the longitudinal axis of the long bone shown in FIG. 2 illustrating various shapes of implants that can be formed therefrom. FIG. 16 shows bone ring 50 being capable of being machined into implants 400 and 500 described above. FIG. 17 shows bone ring 50 being capable of being machined into implants 100 and 500 described above. FIG. 18 shows bone ring 50 being capable of being machined into implants 300 and 600. At least a portion of the medullary canal is preferably included in the interior sides of the implants formed from the bone rings. When possible and where it is desired, at least a portion of the natural curvature of the bone ring is preserved and included in the shape of the implants formed.

Figure 19:
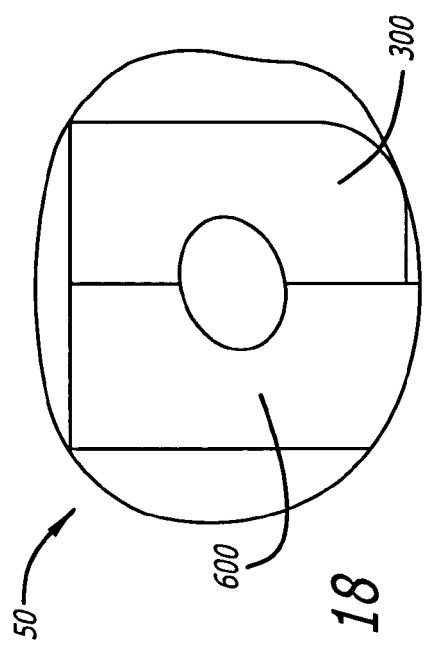
FIG. 19 is a top plan view of a section of diaphyseal bone ring cut across the longitudinal axis of a long bone illustrating the shape of an implant that can be formed therefrom in accordance with another preferred embodiment of the present invention.

While it is preferred to form two implants from each bone ring 50, the present invention is not so limited. For example, FIG. 19 shows bone ring 50 being capable of being machined into a single implant, such as implant 200. It is appreciated that other configuration of implants may be formed in addition to those shown herein without departing from the scope of the present invention.

FIGS. 20A-22B show side elevation views of the diaphyseal bone ring with different configurations of a chamfered tapered end adapted to facilitate the insertion of an implant having a height greater at its a leading end than at its trailing end from the posterior approach to the spine. FIGS. 20A and 20B show bone ring 50' in accordance with a preferred embodiment of the present invention having a chamfer 128 at end 52' that is configured to provide a portion 56' of end 52' having a reduced height that is generally equal to the height of end 54'. The reduced height facilitates introduction into the disc space.

FIGS. 21A and 21B show bone ring 50" in accordance with another preferred embodiment of the present invention. Bone ring 50" is similar to bone ring 50', except that end 52" has a chamfer 130 that is cut at a steeper angle than chamfer 128 to provide a portion 58" of end 52" that has a height that is generally less than the height of end 54".

FIGS. 22A and 22B show bone ring 50''' in accordance with another preferred embodiment of the present invention. Bone ring 50''' is similar to bone ring 50'', except that end 52''' is created by making two cuts at different angles to a mid-longitudinal axis between ends 52''' and 54'''. A first cut is made to form a first chamfer 132 and a second cut is made to form second chamfer 134. A portion 59''' of end 52''' is formed having a height that is generally less than the height of end 54'''.

In any of the embodiments of the present invention, the implant may include, be made of, treated, coated, filled, used in combination with, or have a hollow or medullary canal for containing artificial or naturally occurring materials and/or substances suitable for implantation in the human spine. These materials and/or substances include any source of osteogenesis, bone growth promoting materials, bone, bone derived substances or products, demineralized bone matrix, mineralizing proteins, ossifying proteins, bone morphogenetic proteins, hydroxyapatite, genes coding for the production of bone, and bone including, but not limited to, cortical bone. The implant can include at least in part of materials that are bioabsorbable and/or resorbable in the body such as bone and/or bone growth promoting materials. The implant of the present invention can be formed of a porous material or can be formed of a material that intrinsically participates in the growth of bone from one of adjacent vertebral bodies to the other of adjacent vertebral bodies. Where such implants are for posterior implantation, the trailing ends of such implants may be treated with, coated with, or used in combination with chemical substances to inhibit scar tissue formation in the spinal canal. The implant of the present invention may be modified, or used in combination with materials to make it antibacterial, such as, but not limited to, electroplating or plasma spraying with silver ions or other substance. At least a portion of the implant may be treated to promote bone ingrowth between the implant and the adjacent vertebral bodies. The implant of the present invention may be used in combination with a spinal fixation implant such as any object, regardless of material, that can be inserted into any portion of the spine, such as but not limited to interbody spinal implants, structural bone grafts, mesh, cages, spacers, staples, bone screws, plates, rods, tethers of synthetic cords or wires, or other spinal fixation hardware Although various embodiments of the present invention have been disclosed, they are but preferred embodiments for the purpose of illustration by example and not limitation. It should be understood that any modifications of these teachings as would be known to one of ordinary skill in the art are anticipated and within the scope of the present inventive teachings.

What is claim is:

1. An interbody spinal implant made of cortical bone for insertion at least in part across the height of a disc space between adjacent vertebral bodies of a human spine, the vertebral bodies having an anterior aspect and a posterior aspect, said implant comprising:

a leading end for insertion first into the disc space, a trailing end opposite said leading end, said implant having a length along a mid-longitudinal axis of said implant from said leading end to said trailing end;

opposed upper and lower portions between said leading and trailing ends adapted to be placed at least in part within and across the height of the disc space to contact and support the adjacent vertebral bodies, said opposed upper and lower portions having a maximum height therebetween, said upper and lower portions being non-arcuate along at least a portion of the length of said implant;

an interior side, an exterior side opposite said interior side, and a maximum width therebetween greater than said maximum height, said maximum width of said implant being less than one-half of the width of the adjacent vertebral bodies into which said implant is adapted to be inserted, said interior and exterior sides connecting said upper and lower portions and said leading and trailing ends, said interior side and said exterior side each being at least in part straight along at least a portion of the length of said implant, said leading end being asymmetrical from side to side, said leading end and said trailing end each being at least in part curved from side to side, said interior side adapted to be oriented toward an interior side of another implant when inserted within the disc space;

said implant being manufactured from a bone ring obtained from a major long bone of a human having a medullary canal, said implant including at least 40 percent of the bone ring from which it is being formed, said interior side of said implant including at least a portion of the medullary canal so that when said implant is placed side by side another implant having an interior side including at least a portion of a medullary canal a passage is formed adapted to hold bone growth promoting material for permitting for the growth of bone from vertebral body to vertebral body through said passage.

2. The implant of claim 1, wherein said leading end includes a generally straight portion from side to side.

3. The implant of claim 2, wherein said straight portion of said leading end is generally oriented at 90 degrees to the mid-longitudinal axis of said implant.

4. The implant of claim 1, wherein at least a portion of said leading end has a reduced height to facilitate insertion of said implant between the two adjacent vertebral bodies.

5. The implant of claim 1, wherein said trailing end is at least in part straight from side to side.

6. The implant of claim 1, wherein said trailing end is configured in the shape of a half circle from side to side.

7. The implant of claim 1, wherein said trailing end is asymmetrical side to side.

8. The implant of claim 1, wherein the trailing end is adapted to conform from side to side to at least a portion of the peripheral contour of at least one of the anterior and posterior aspects of the vertebral bodies adjacent a disc space into which said implant is inserted.

9. The implant of claim 1, wherein at least one of said interior and exterior sides is at least in part oriented generally parallel to the mid-longitudinal axis of said implant.

10. The implant of claim 1, wherein said interior and exterior sides are at least in part generally parallel one another.

11. The implant of claim 1, wherein at least a portion of said upper and lower surfaces are in an angular relationship to each other from trailing end to leading end for allowing angulation of the adjacent vertebral bodies relative to each other.

12. The implant of claim 1, wherein said upper and lower surfaces include at feast one opening in communication with one another to permit for the growth of bone from vertebral body to vertebral body through said implant.

13. The implant of claim 1, wherein said implant has a maximum length less than and approximating the posterior to anterior depth of the vertebral bodies.

14. The implant of claim 1, further comprising a bone engaging surface formed on the exterior of at least said upper and lower portions for engaging the adjacent vertebral bodies, said bone engaging surface including at least one of a protrusion, a ratchet, a spike, a spline, surface roughenings, and knurling.

15. The implant of claim 1, wherein said implant comprises at least in part of a bone growth promoting material.

16. The implant of claim 15, wherein said bone growth promoting material is selected from one of bone, bone derived products, demineralized bone matrix, mineralizing proteins, ossifying proteins, bone morphogenetic protein, hydroxyapatite, and genes coding for the production of bone.

17. The implant of claim 1, in combination with a bone growth promoting material.

18. The implant of claim 17, wherein said bone growth promoting material is selected from one of bone, bone derived products, demineralized bone matrix, mineralizing proteins, ossifying proteins, bone morphogenetic protein, hydroxyapatite, and genes coding for the production of bone.

19. The implant of claim 1, wherein said implant is treated with a bone growth promoting substance.

20. The implant of claim 1, wherein said implant is at least in part resorbable.

21. The implant of claim 1, in combination with a chemical substance adapted to inhibit scar formation.

22. The implant of claim 1, in combination with an anti-microbial material.

23. The implant of claim 1, wherein at least a portion of said implant is treated to promote bone ingrowth between said implant and said adjacent vertebral bodies.

24. The implant of claim 1, further in combination with at least one spinal fixation implant.

25. A pair of interbody spinal implants made of a bone composite material for insertion at least in part across the height of a disc space between adjacent vertebral bodies of a human spine, the vertebral bodies having an anterior aspect, a posterior aspect, and a depth therebetween, each of said implants comprising:

a leading end for insertion first into the disc space, a trailing end opposite said leading end, said implant having a length along a mid-longitudinal axis of said implant from said leading end to said trailing end, said length of said implant being greater than one half the depth of the vertebral bodies adjacent the disc space into which said implant is adapted to be inserted;

opposed upper and lower portions between said leading and trailing ends adapted to be placed at least in part within and across the height of the disc space to contact and support the adjacent vertebral bodies, said opposed upper and lower portions having a maximum height therebetween, said upper and lower portions being non-arcuate along at least a portion of the length of said implant;

an interior side, an exterior side opposite said interior side, and a maximum width therebetween greater than said maximum height, said maximum width of said implant being less than approximately one-half of the width of the adjacent vertebral bodies into which said implant is adapted to be inserted, said interior and exterior sides connecting said upper and lower portions and said leading and trailing ends, said interior side and said exterior side each being at least in part straight along at least a portion of the length of said implant, said leading end being asymmetrical from side to side, said leading end and said trailing end each being at least in part curved from side to side, said interior side adapted to be oriented toward an interior side of another implant when inserted within the disc space; and said implant being manufactured from a bone composite material, said interior side of said implant including a recess, said interior side of said implant including a recess so that when said implant is placed side by side another implant having an interior side including a recess a passage is formed adapted to hold bone growth promoting material for permitting for the growth of bone from vertebral body to vertebral body through said passage; and the combined width of said pair of said implants being greater than one half the width of the adjacent vertebral bodies into which said implants are adapted to be inserted.

26. The implant of claim 25, wherein said bone composite material includes at least one of cortical bone fibers, bone filaments, bone particles and bone dust.

27. The implant of claim 25, further comprising a binding material.

28. The implant of claim 27, wherein said binding material is at least one of bioactive and bioresorbable.

29. The implant of claim 25, wherein said leading end includes a generally straight portion from side to side.

30. The implant of claim 29, wherein said straight portion of said leading end is generally oriented at 90 degrees to the mid-longitudinal axis of said implant.

31. The implant of claim 25, wherein at least a portion of said leading end has a reduced height to facilitate insertion of said implant between the two adjacent vertebral bodies.

32. The implant of claim 25, wherein said trailing end is at least in part straight from side to side.

33. The implant of claim 25, wherein said trailing end is configured in the shape of a half circle from side to side.

34. The implant of claim 25, wherein said trailing end is asymmetrical side to side.

35. The implant of claim 25, wherein the trailing end is adapted to conform from side to side to at least a portion of the peripheral contour of at least one of the anterior and posterior aspects of the vertebral bodies adjacent a disc space into which said implant is inserted.

36. The implant of claim 25, wherein at least one of said interior and exterior sides is at least in part oriented generally parallel to the mid-longitudinal axis of said implant.

37. The implant of claim 25, wherein said interior and exterior sides are at least in part generally parallel one another.

38. The implant of claim 25, wherein at least a portion of said upper and lower surfaces are in an angular relationship to each other from trailing end to leading end for allowing angulation of the adjacent vertebral bodies relative to each other.

39. The implant of claim 25, wherein said upper and lower surfaces include at least one opening in communication with one another to permit for the growth of bone from vertebral body to vertebral body through said implant.

40. The implant of claim 25, wherein said implant has a maximum length less than and approximating the posterior to anterior depth of the vertebral bodies.

41. The implant of claim 25, further comprising a bone engaging surface formed on the exterior of at feast said upper and lower portions for engaging the adjacent vertebral bodies, said bone engaging surface including at least one of a protrusion, a ratchet, a spike, a spline, surface roughenings, and knurling.

42. The implant of claim 25, wherein said implant comprises at least in part of a bone growth promoting material.

43. The implant of claim 42, wherein said bone growth promoting material is selected from one of bone, bone derived products, demineralized bone matrix, mineralizing proteins, ossifying proteins, bone morphogenetic protein, hydroxyapatite, and genes coding for the production of bone.

44. The implant of claim 25, in combination with a bone growth promoting material.

45. The implant of claim 44, wherein said bone growth promoting material is selected from one of bone, bone derived products, demineralized bone matrix, mineralizing proteins, ossifying proteins, bone morphogenetic protein, hydroxyapatite, and genes coding for the production of bone.

46. The implant of claim 25, wherein said implant is treated with a bone growth promoting substance.

47. The implant of claim 25, wherein said implant is at least in part resorbable.

48. The implant of claim 25, in combination with a chemical substance adapted to inhibit scar formation.

49. The implant of claim 25, in combination with an antimicrobial material.

50. The implant of claim 25, wherein at least a portion of said implant is treated to promote bone ingrowth between said implant and said adjacent vertebral bodies.

51. The implant of claim 25, further in combination with at least one spinal fixation implant.

52. A pair of interbody spinal implants made of cortical bane for insertion at least in part into the same implantation space formed across the height of a disc space between adjacent vertebral bodies of a human spine, the vertebral bodies having an anterior aspect and a posterior aspect and a depth therebetween, each of said implants comprising:
    a leading end for insertion first into the disc space, a trailing end opposite said leading end, and a length from said leading end to said trailing end;
    opposed upper and lower portions between said leading and trailing ends adapted to be placed at least in part within and across the height of the disc space to contact and support the adjacent vertebral bodies, said upper and lower portions defining a height of each of said implants, said upper and lower portions being non-arcuate along at least a portion of the length of each of said implants; and
    opposite sides between said upper portion and said lower portion, and between said leading and trailing ends, said opposite sides defining a width of each of said implants, said leading end being configured in the shape of a portion of a circle from one of said opposite sides to another one of said opposite sides, the circle having a radius greater than the width of each of said implants;
    each of said implants being manufactured from a bone ring obtained from a major long bone of a human being having a medullary canal, one of said opposite sides of each of said implants including at least a portion of the medullary canal so that when said pair of implants are placed side-by-side in the same disc space a passage is formed adapted to hold bone growth promoting material for permitting for the growth of bone from vertebral body to vertebral body through each of said implants;
    said leading ends of said implants forming part of the same circle when inserted into the same implantation space.

53. The pair of implants of claim 52, wherein each of said implants has a maximum width between said opposite sides that is less than one-half of the width of the adjacent vertebral bodies into which each of said implants is adapted to be inserted.

54. The pair of implants of claim 52, wherein at least a portion of said leading end of each of said implants has a reduced height to facilitate insertion of each of said implants between the two adjacent vertebral bodies.

55. The pair of implants of claim 52, wherein said trailing end of at least one of said implants has a radius of curvature of a second circle from side to side.

56. The pair of implants of claim 55, wherein the radius of curvature said trailing end is greater than the radius of curvature of the leading end of said at least one of said implants.

57. The pair of implants of claim 52, wherein each of said implants has a mid-longitudinal axis along the length, at least one of said opposite sides of at least one of said implants being at least in part oriented generally parallel to the mid-longitudinal axis of said at least one of said implants.

58. The pair of implants of claim 52, wherein said opposite sides of at least one of said implants are at least in part generally parallel one another.

59. The pair of implants of claim 52, wherein at least a portion of said upper and lower portions of at least one of said implants are in an angular relationship to each other from trailing end to leading end for allowing angulation of the adjacent vertebral bodies relative to each other.

60. The pair of implants of claim 52, wherein at least one of said implants has a maximum length less than and approximating the posterior to anterior depth of the vertebral bodies.

61. The pair of implants of claim 52, wherein at least one of said implants further comprises a bone engaging surface formed on the exterior of at least said upper and lower portions for engaging the adjacent vertebral bodies, said bone engaging surface including at least one of a protrusion, a ratchet, surface roughenings, and knurling.

62. The pair of implants of claim 52, in combination with a bone growth promoting material.

63. The pair of implants of claim 62, wherein said bane growth promoting material is selected from one of bone, bone derived products, demineralized bone matrix, mineralizing proteins, ossifying proteins, bone morphogenetic protein, hydroxyapatite, and genes coding for the production of bone.

64. The pair of implants of claim 52, wherein at least one of said implants is treated with a bone growth promoting substance.

65. The pair of implants of claim 52, wherein at least one of said implants is at least in part resorbable.

66. The pair of implants of claim 52, in combination with a chemical substance adapted to inhibit scar formation.

67. The pair of implants of claim 52, in combination with an antimicrobial material.

68. The pair of implants of claim 52, wherein at least a portion of at least one of said implants is treated to promote bone ingrowth between said at least one of said implants and said adjacent vertebral bodies.

69. The pair of implants of claim 52, wherein said first and second implants are mirror images of one another.

70. An interbody spinal implant made of cortical bone for insertion at least in part into an implantation space formed across the height of a disc space between adjacent vertebral bodies of a human spine, the vertebral bodies having an anterior aspect and a posterior aspect and a depth therebetween, said implant comprising:
    a leading end for insertion first into the disc space and a trailing end opposite said leading end, said implant having a length from said leading end to said trailing end;
    opposed upper and lower portions between said leading and trailing ends adapted to be placed at least in part within and across the height of the disc space to contact and support the adjacent vertebral bodies, said upper and lower portions defining a height of said implant, said upper and lower portions being non-arcuate along at least a portion of the length of said implant; and opposite sides between said upper portion and said lower portion, and between said leading and trailing ends, said opposite sides defining a width of said implant, each of said sides being at least in part straight along at least a portion of the length of said implant, said leading end being configured in the shape of a portion of a circle from one of said opposite sides to another one of said opposite sides, the circle having a radius greater than the width of said implant, the width of said implant being less than one-half the width of the adjacent vertebral bodies into which said implant is adapted to be inserted;

said implant being manufactured from a bone ring obtained from a major long bone of a human being having a medullary canal, one of said opposite sides of each of said implants including at least a portion of the medullary canal so that when said pair of implants are placed side-by-side in the same disc space a passage is formed adapted to hold bone growth promoting material for permitting for the growth of bone from vertebral body to vertebral body through said implant.

71. The implant of claim 70, wherein said implant is adapted to be inserted side by side a second implant into the disc space between the adjacent vertebral bodies, said second implant having a leading end configured in the shape of a portion of a circle from side to side, the circle having a radius greater than the width of said second implant.

72. The implant of claim 70, wherein at least a portion of said leading end has a reduced height to facilitate insertion of said implant between the two adjacent vertebral bodies.

73. The implant of claim 70, wherein said trailing end has a radius of curvature of a second circle from side to side.

74. The implant of claim 73, wherein the radius of curvature said trailing end is greater than the radius of curvature of the leading end of said implant.

75. The implant of claim 70, wherein said implant has a mid-longitudinal axis along the length, at least one of said opposite sides being at least in part oriented generally parallel to the mid-longitudinal axis of said implant.

76. The implant of claim 70, wherein said opposite sides are at least in part generally parallel one another.

77. The implant of claim 70, wherein at least a portion of said upper and lower portions are in an angular relationship to each other from trailing end to leading end for allowing angulation of the adjacent vertebral bodies relative to each other.

78. The implant of claim 70, wherein said implant has a maximum length less than and approximating the posterior to anterior depth of the vertebral bodies.

79. The implant of claim 70, further comprising a bone engaging surface formed on the exterior of at least said upper and lower portions for engaging the adjacent vertebral bodies, said bone engaging surface including at least one of a protrusion, a ratchet, surface roughenings, and knurling.

80. The implant of claim 70, in combination with a bone growth promoting material.

81. The implant of claim 80, wherein said bone growth promoting material is selected from one of bone, bone derived products, demineralized bone matrix, mineralizing proteins, ossifying proteins, bone morphogenetic protein, hydroxyapatite, and genes coding for the production of bone.

82. The implant of claim 70, wherein said implant is treated with a bone growth promoting substance.

83. The implant of claim 70, wherein said implant is at least in part resorbable.

84. The implant of claim 70, in combination with a chemical substance adapted to inhibit scar formation.

85. The implant of claim 70, in combination with an antimicrobial material.

86. The implant of claim 70, wherein at least a portion of said implant is treated to promote bone ingrowth between said implant and said adjacent vertebral bodies.

* * * * *

UNITED STATES PATENT AND TRADEMARK OFFICE
CERTIFICATE OF CORRECTION

PATENT NO. : 7,611,536 B2  Page 1 of 1
APPLICATION NO. : 11/338395
DATED : November 3, 2009
INVENTOR(S) : Gary K. Michelson It is certified that error appears in the above-identified patent and that said Letters Patent is hereby corrected as shown below:

Title Page 2, Item (56) References Cited, Column 2:
U.S. Patent Documents, Line 20: change "Aebl" to -- Aebi --;
Foreign Patent Documents, Line 5: change "EP 2703580' to -- FR 2703580 --; and
Other Publications, Line 5: change "Cyllnrical" to -- Cylindrical --.

Column 10:
Line 60: change "feast" to -- least --.

Column 12:
Line 11: change "halt" to -- half --; and
Line 59: change "feast" to -- least --.

Column 13:
Line 25: change "bane" to -- bone --.

Column 14:
Line 31: change "bane" to -- bone --.

Signed and Sealed this

Sixteenth Day of February, 2010

David J. Kappos
*Director of the United States Patent and Trademark Office*